USO10441357B2

(12) United States Patent
Moeskops et al.

(10) Patent No.: US 10,441,357 B2
(45) Date of Patent: Oct. 15, 2019

(54) DEVICE FOR CUTTING HAIR

(71) Applicant: KONINKLIJKE PHILIPS N.V., Eindhoven (NL)

(72) Inventors: Bastiaan Wilhelmus Maria Moeskops, Eindhoven (NL); Mark Thomas Johnson, Eindhoven (NL); Rieko Verhagen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 261 days.

(21) Appl. No.: 14/401,552

(22) PCT Filed: May 15, 2013

(86) PCT No.: PCT/IB2013/053972
§ 371 (c)(1),
(2) Date: Nov. 17, 2014

(87) PCT Pub. No.: WO2013/175355
PCT Pub. Date: Nov. 28, 2013

(65) Prior Publication Data
US 2015/0164589 A1    Jun. 18, 2015

Related U.S. Application Data

(60) Provisional application No. 61/649,985, filed on May 22, 2012.

(51) Int. Cl.
*A61B 18/20* (2006.01)
*B23K 26/06* (2014.01)
*A45D 7/00* (2006.01)
*A61B 18/00* (2006.01)
(Continued)

(52) U.S. Cl.
CPC ........ *A61B 18/203* (2013.01); *B23K 26/0648* (2013.01); *A45D 2007/007* (2013.01); *A61B 2018/00601* (2013.01); *A61B 2018/00904* (2013.01); *A61B 2090/036* (2016.02); *B23K 2103/32* (2018.08); *B23K 2103/50* (2018.08); *F04C 2270/041* (2013.01)

(58) Field of Classification Search
CPC ........... A61F 2009/00872; A61F 9/008; A61B 18/203; A45D 24/22
USPC ..................... 606/2–19; 607/86–94
See application file for complete search history.

(56) References Cited

U.S. PATENT DOCUMENTS 5,533,266 A * 7/1996 Kelman ............... A61B 18/203
                                                132/200
5,993,440 A * 11/1999 Ghassemi ............... B26B 19/00
                                                30/41.5
(Continued)

FOREIGN PATENT DOCUMENTS

EP    1933753 B1    6/2008
JP    05509025 A    12/1993
(Continued)

*Primary Examiner* — Carl H Layno
*Assistant Examiner* — Dacheng Xie

(57) ABSTRACT

A cutting head for a device for cutting hair is disclosed. The cutting head has an optical system configured to direct a laser beam along an optical axis across a cutting zone within the cutting head. The optical system has a variable focus lens configured to control the position of the focal point of the laser beam along the optical axis within the cutting zone.

15 Claims, 4 Drawing Sheets

(51) Int. Cl.
*A61B 90/00* (2016.01)
*B23K 103/00* (2006.01)

(56) References Cited

U.S. PATENT DOCUMENTS

| | | | | |
|---|---|---|---|---|
| 7,101,365 B1* | 9/2006 | Sharon | ............... | A61B 18/203 |
| | | | | 606/10 |
| 2006/0200116 A1* | 9/2006 | Ferren | ............... | A61B 18/203 |
| | | | | 606/9 |
| 2008/0072437 A1* | 3/2008 | Michel | ............... | A45D 24/22 |
| | | | | 30/201 |
| 2008/0215038 A1* | 9/2008 | Bakker | ............... | A61B 18/203 |
| | | | | 606/9 |
| 2009/0264872 A1 | 10/2009 | Van Hal | | |
| 2009/0294668 A1* | 12/2009 | Bowers | ............... | G02B 27/40 |
| | | | | 250/336.1 |
| 2014/0214014 A1* | 7/2014 | Yamazaki | ............... | A45D 26/00 |
| | | | | 606/9 |

FOREIGN PATENT DOCUMENTS

| | | | |
|---|---|---|---|
| JP | 10501464 | A | 12/1996 |
| JP | 2000316998 | A | 11/2000 |
| JP | 2009101183 | A | 5/2009 |
| WO | 9216338 | A1 | 10/1992 |
| WO | 9533600 | A1 | 12/1995 |
| WO | 2004081549 | A1 | 9/2004 |
| WO | 2005102201 | A1 | 11/2005 |
| WO | 2007013008 | A1 | 2/2007 |
| WO | 2007039853 | A1 | 4/2007 |
| WO | 2008137948 | A1 | 11/2008 |
| WO | 2010106480 | A1 | 9/2010 |
| WO | 2011121536 | A1 | 10/2011 |

* cited by examiner

DEVICE FOR CUTTING HAIR

This application is the U.S. National Phase application under 35 U.S.C. § 371 of International Application No. PCT/IB2013/053972, filed on May 15, 2013, which claims the benefit of U.S. Provisional Application No. 61/649,985 filed on May 22, 2012. These applications are hereby incorporated by reference herein.

FIELD OF THE INVENTION

This invention relates to a device for cutting hair.

BACKGROUND OF THE INVENTION

It is known to provide a shaver or razor that relies on a laser for cutting hair rather than an arrangement of cutting blades. Shavers without blades have fewer moving parts and so wear is reduced, which provides an advantage over mechanical shavers. Furthermore, the use of a laser can reduce skin irritation as there are no sharp objects that contact the skin surface. Laser shavers work by optical absorption in which hair exposed to a laser beam absorbs the energy of the beam, causing it to be vaporised and/or severed.

Shaving performance is typically measured by two criteria—closeness of shave and irritation of the skin. Therefore, a good performing shaver should minimise the remaining hair length by positioning the laser as close as possible to the skin. However, this may cause more skin irritation if heat and energy from the laser is incident on the skin. It is necessary to protect the skin from contact with the laser beam to avoid damaging or irritating the skin being shaved. Hair trimmers or groomers are used to trim hair to a constant length, so although closeness is not a major performance factor, uniformity of remaining hair length is desirable.

It is known, for example from WO 95/33600, to generate a laser beam that is positioned parallel to the skin and perpendicular to the stroke direction to cut hairs as the shaver is moved over the skin. However, Gaussian theory dictates that laser beams have a natural intensity variation along their length. Beams will have a focal point where the laser beam has maximum intensity (power per unit area) and minimum width, meaning the focal point is the most effective part of the laser beam for severing hair by optical absorption. On the other hand, parts of the laser beam furthest from the focal point will have a larger width and therefore a more distributed intensity and will not be as effective at severing hair because the energy of the laser beam is incident over a larger area of hair. Therefore, there is a variation in hair severing performance along the optical axis of a laser beam and this may result in uneven hair severing and non-uniform closeness. Due to the natural divergence of Gaussian laser beams it is impossible to achieve a uniform beam thickness along an optical axis.

SUMMARY OF THE INVENTION

It is an object of this invention to provide a device for cutting hair that overcomes or substantially alleviates the problems described above.

According to the invention, there is provided a cutting head for a device for cutting hair, comprising an optical system configured to direct a laser beam along an optical axis across a cutting zone in the cutting head, the optical system comprising a variable focus lens configured to control the position of the focal point of the laser beam along the optical axis within the cutting zone.

Being able to move the focal point of the laser beam along the optical axis allows the high intensity part of the laser beam to be moved across the cutting zone, ensuring that all of the hairs that enter the cutting zone are subjected to the high intensity focal point of the beam. In this way, fewer, or none of the hairs that enter into the cutting zone will only be subjected to low intensity parts of the beam, improving the closeness and uniformity of cut.

Advantageously, the optical system is configured such that during movement of the position of the focal point of the laser beam along the optical axis within the cutting zone, the position of the optical axis is not altered.

Maintaining the position of the optical axis ensures that the cutting height remains constant which is important for uniformity of cut. If the optical axis were to move, the cutting laser beam would also move, varying the cutting height.

The optical system may comprise a first reflective element to direct the laser beam across the cutting zone.

The reflective element means that the laser beam generator does not need to be positioned in line with the cutting optical axis and provides a space for the variable focus lens. This arrangement is possible because a property of Gaussian beams is that they maintain their optical properties after reflection.

Preferably, the first reflective element may be positioned such that, during use, the optical axis across the cutting zone is parallel to the skin of a user.

The laser beam may be parallel to the skin of a user to maximise the width of the cutting zone.

During use, the variable focus lens may be positioned between a laser generator in the device for cutting hair and the first reflective element.

Locating the variable focus here is possible because the optical properties of the laser beam are maintained when the beam is reflected. This arrangement also reduces the size of the cutting head because the variable focus lens need not be positioned in line with the cutting laser beam axis.

The cutting head may further comprise a spacer, positioned adjacent to the cutting zone to contact a user's skin during use to maintain spacing between a user's skin and the laser beam in the cutting zone.

A spacer can maintain a separation between the laser cutting beam and the surface of the skin, while allowing hairs to protrude through or past the spacer so that the hairs can be cut. Maintaining separation between the laser beam and the skin is important for minimising the irritation caused to the skin.

In one embodiment, the optical system may comprise a second reflective element positioned on the opposite side of the cutting zone to the first reflective element, to direct the laser beam away from the cutting zone.

The laser beam may be directed away from the skin after cutting to avoid inadvertent heating of the cutting head assembly or damage to the skin.

In another embodiment, the optical system may comprise a second reflective element configured to direct the laser beam back across the cutting zone, such that a second laser beam is present in the cutting zone for cutting hair.

Having multiple laser beams in the cutting zone will improve the performance of the shaver because there is less opportunity for hairs to pass through the cutting zone without being subject to the focal point of at least one laser beam. Therefore, adequate shaving or trimming performance can be achieved with fewer passes over the skin.

According to another aspect of the invention, there is provided a device for cutting hair comprising a cutting head as described above and a controller to control the variable focus lens.

The controller allows the variable focus lens to be controlled automatically and/or by user input.

The controller may be configured to control the variable focus lens to control the focal point of the laser beam along the optical axis, across the cutting zone, in an oscillating motion.

This scanning motion is effective at ensuring a uniform and close cut over the skin of a user. Moving the focal point across the cutting zone will ensure that more of the hairs that enter the cutting zone are subjected to the high intensity region around the focal point.

The controller may be configured to control the variable focus lens to control the focal point of the laser beam along the optical axis so that the oscillating motion is such that the dwell time of the focal point at any position along the optical axis is substantially constant.

Controlling the oscillating motion of the focal point of the cutting laser beam so that there is substantially equal dwell time across the cutting zone ensures even cutting performance and improves uniformity.

The device for cutting hair may further comprise a hair sensor, wherein the hair sensor is configured to detect the position of a hair of the user in the cutting zone and the controller is configured to move the focal point of the laser beam to coincide with said detected hair.

The hair sensor may allow the shaver to be configured to target each individual hair or group of hairs that enter into the cutting zone. This may further improve the uniformity of cut as more hairs will be subjected to the focal point of the laser beam.

According to another aspect of the invention, there is provided a device for cutting hair comprising a cutting head as described above.

According to another aspect of the invention, there is provided a device for cutting hair having a plurality of cutting heads as described above.

A plurality of cutting heads would improve performance still further because each movement of the device over the skin of a user will result in multiple cutting heads cutting the hairs. This may be used to cover a larger area and/or to shave the same area multiple times to ensure a close and uniform cut.

According to another aspect of the invention, there is provided a method of controlling a device for cutting hair, comprising the steps of;

directing a laser beam across a cutting zone along an optical axis, and controlling a variable focus lens to control the position of the focal point of the laser beam along the optical axis in the cutting zone.

The variable focus lens may be controlled to cause the position of the focal point of the laser beam to oscillate along the optical axis, across the cutting zone.

BRIEF DESCRIPTION OF THE DRAWINGS

Embodiments of the invention will now be described, by way of example only, with reference FIGS. 2 to 5 of the accompanying drawings, in which.

DETAILED DESCRIPTION OF THE EMBODIMENTS

Figure 1:
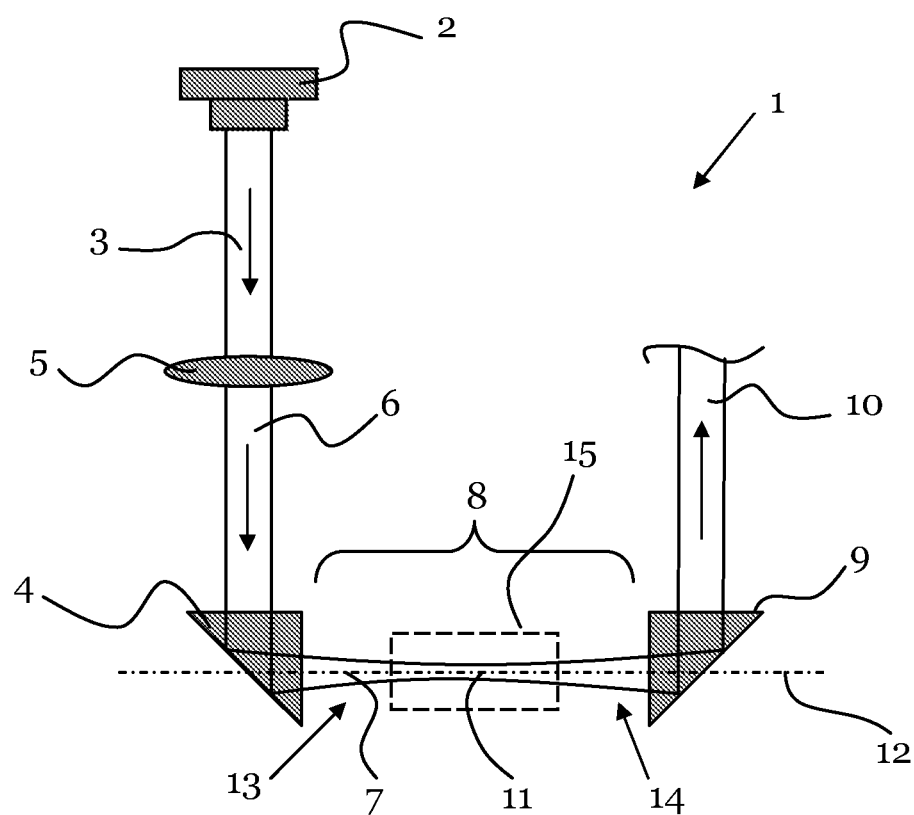
FIG. 1 shows a schematic diagram of an optical system for a cutting head of a laser shaver, as is known in the art.

FIG. 1 shows a schematic diagram of an optical system 1 for a cutting head of a laser shaver as is known in the art. The optical system 1 comprises a laser generator 2, such as a diode. The diode 2 emits a laser beam 3 towards a first reflective element 4 via a collimating lens 5 that reduces or eliminates divergence of the beam. The collimated beam 6 is then reflected by the first reflective element 4 through 90 degrees and the beam 7 travels across a cutting zone 8 where hairs are received to be cut by optical absorption caused by the cutting laser beam 7. A second reflective element 9 is positioned on the opposite side of the cutting zone 8 to reflect the cutting laser beam 7 along an exit path 10 that travels away from the cutting zone 8. The exit beam 10 may then be absorbed within an energy dissipater or similar device to prevent damage being caused by the energy of the remaining laser beam 10.

Between the first and second reflective elements 4, 9 the cutting laser beam 7 will conform to Gaussian theory and will comprise a 'focal point' 11, or waist, located somewhere along the optical axis 12 of the beam 7. The focal point 11 is the position of maximum intensity and minimum width and the most effective part of the beam 7 for severing hair because the laser beam energy is concentrated on a smaller area of the hair to be severed, increasing the rate of optical absorption. The regions 13, 14 either side of the waist 11 have a larger beam width and lower intensity so are less effective for severing hair because the laser beam energy is distributed over a larger area of the hair. This arrangement may lead to an undesirable variation in cutting performance across the cutting zone 8 as the focal point 11 of the laser beam 7 severs hairs more cleanly and at a different length to the other parts 13, 14 of the cutting laser beam 7.

Gaussian beam theory can be used to determine the natural variation in intensity along a beam by considering the change in beam width (cross-sectional area) caused by divergence. The divergence of a perfect Gaussian laser beam is defined by the following equation:

$$w(z) = w_0 \sqrt{\left[1 + M^2 \left(\frac{z^2}{z_R^2}\right)\right]}$$

Wherein w(z) is the beam radius at a distance z from the beam waist (focal point), $w_0$ is the radius of the beam waist and $z_R$ is the Rayleigh range, while $M^2$ is the beam propagation factor which is a measure of beam quality. The Rayleigh range ($z_R$) of a laser beam is defined as the distance over which the beam surface area is doubled and is described by the following equation:

$$z_R = \frac{\pi \cdot w_0^2}{\lambda}$$

Where λ is the wavelength of the laser beam.

The Rayleigh range is the portion of the beam with the highest intensity, making it the most effective part of the beam for cutting hair because the energy of the laser beam is focussed on a smaller area of the hair. The Rayleigh range, or high intensity region, is represented by the dotted line 15 in FIG. 1 which is in a fixed position. Regions 13, 14 of the beam outside of the Rayleigh range 15 have a larger beam width with a less concentrated energy distribution. Therefore, the hair cutting characteristics of these regions will not be as effective at cutting hair as in the Rayleigh range. A well designed laser shaver should not generate a laser beam that is significantly more powerful than required to sever hairs because of power requirements, excessive heat and skin irritation. Therefore, it is important to identify the high intensity region 15 of a cutting beam and utilise it effectively in a laser shaver.

Figure 2:
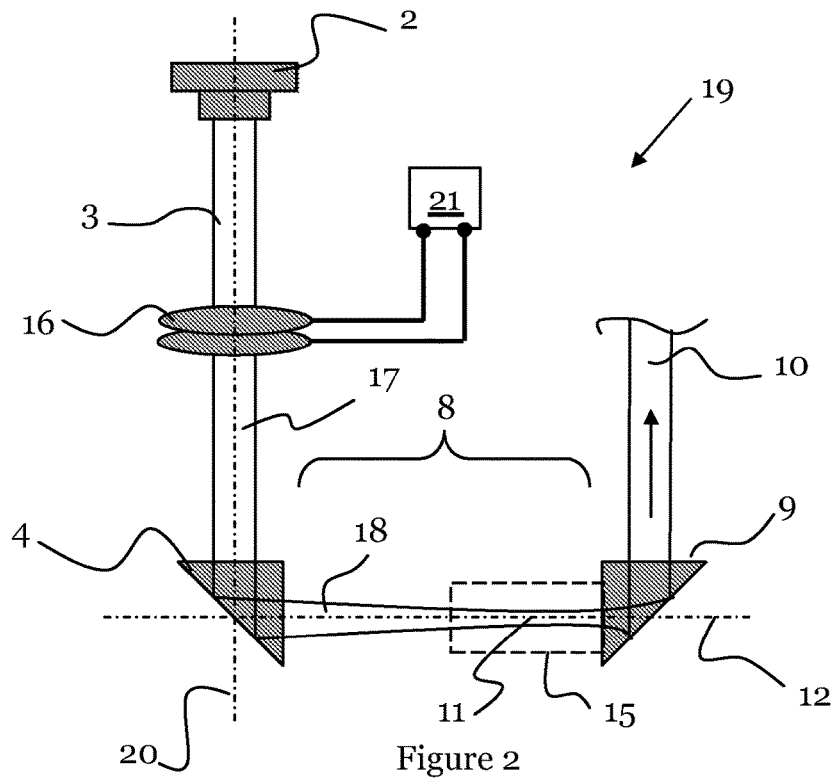
FIG. 2 shows a schematic diagram of an optical system for a cutting head.

FIG. 2 shows a schematic diagram of an optical system 19 of a cutting head according to the invention. Instead of a collimating lens, as described with reference to FIG. 1, the optical system 19 of FIG. 2 comprises a variable focus lens 16.

The variable focus lens 16 receives the laser beam 3 from the diode 2 and is configured to adjust the focal point of the variable focus beam 17 that is incident on the first reflective element 4 in response to some control input 21. The control input may be from a processor or controller or from manual adjustment of the lens by a user. The controller may be configured to respond to user inputs or act on preset functions that generate pre-determined movements of the variable focus lens 16. The lens may comprise an actuator (not shown) that is controlled by the controller 21 to actuate the focus alteration but this depends on the type of variable focus lens being used, as explained later.

The controller may be a microprocessor and may be provided with an electronic memory to enable it to store commands or instructions. The type of controller and the type of output required from the controller will depend on the kind of variable focus lens used.

The first reflective element 4 reflects the variable focus beam 17 through 90 degrees and across the cutting zone 8, along the optical axis 12, to form a cutting laser beam 18. It is important that the variable focus lens 16 only moves the focal point of the variable focus beam 17 along its optical axis 20 so that the optical axis 12 of the cutting beam 18 remains in a fixed position. The fixed position of the optical axis 12 of the cutting laser beam 18 means that the cutting height remains constant and the laser beam remains parallel to the skin of the user during use. In this embodiment, a second reflective element 9 is positioned on the opposite side of the cutting zone 8 to the first reflective element 4 and reflects the cutting laser beam through 90 degrees and away from the cutting zone 8 along the exit beam 10, as before.

Operation of the variable focus lens 16 results in movement of the focal point of the variable focus beam 17 along the optical axis 20 which in turn, once reflected by the first reflective element 4, causes the position of the focal point 11 of the cutting laser beam 18 to be moved along the optical axis 12 in either direction. Therefore, the portion of the cutting laser beam 18 within the high intensity region 15 that is effective at severing hairs is moveable along the optical axis 12 by controlling the variable focus lens 16. This movement may be used to generate a cutting laser beam with a constantly moving focal point that scans back and forth across the cutting zone as the shaver is moved over the skin. This allows the laser shaver to effectively cover a larger area in less time or with fewer passes. Furthermore, constant movement of the focal point 11 of the cutting laser beam 18 will improve the uniformity of the remaining hair length by eliminating the variations in cutting intensity and cutting height across the cutting zone 8.

It is possible to control the variable focus lens 16 to create other movements of the focal point. For example the variable focus lens may be controlled to cause the focal point 11 of the cutting laser beam 18 to oscillate back and forth across the cutting zone 8 in a sinusoidal or symmetric saw-tooth motion. However, it is important to ensure that the dwell time at any point across the cutting zone is substantially constant so that no area is subject to more cutting action than another area. To achieve this, the oscillating motion, sinusoidal, saw-tooth or otherwise, may have constant and identical uniform velocity in both directions.

The moveable focal point of the cutting laser beam may be used to allow the user to choose to position the focal point at an end of the cutting zone 8 when cutting hair close to the edge of a region of hair which should not be removed, such as a moustache, partial beard or sideburns. This can result in the edge of the region being cleanly cut to make a distinct divide between cut hair and uncut hair. Furthermore the user may choose to position the focal point at one of the ends of the cutting zone 8 when cutting hair on a part of the face that is smaller than the width of the cutting zone such as between upper lip and nose.

Different types of variable focus lens that are known in the art will now be described, any of which may be applicable for the optical system described with reference to FIG. 2.

Mechanically actuated adjustable lenses are well known and usually comprise rotational or linear displacement to alter the position of the focal point of the beam(s) passing through them. They may have electric actuators or components that may be moved by a user, such as a wheel or lever to actuate the lens adjustment.

Fluid focus lenses use the electro-wetting principle; the angle of contact between a drop of liquid, such as water or oil, and a thin film deposited on a substrate is changed by applying a voltage to a thin electrode positioned between the substrate and the thin film. The shape of the liquid drop, and hence the surface profile of the liquid, is changed by the change in the angle of contact. In this manner, a lens with a varying focal length can be realised.

Liquid crystal lenses, such as switchable GRIN (gradient index) lenses, exploit the property that the refractive index of a liquid crystal material is different along an axis and perpendicular to that axis through the liquid crystal molecules. For this reason, the refractive index of a lens comprising a lens shaped cavity filled with liquid crystal material can be changed by rotating the orientation of the liquid crystal molecules. The orientation of the liquid crystal molecules can be changed by applying a voltage across the lens cavity, whereby a lens with variable focus is realised.

Electrophoretic based variable focus lenses comprise charged particles in a liquid. This class of lens exploits the property that the refractive index of the charged particles can be chosen to be different to that of the liquid. The refractive index of a lens comprising a lens shaped cavity filled with electrophoretic particles in a liquid of different refractive index can be changed by changing the concentration of particles in the liquid in the lens cavity. The concentration of particles in the liquid in the lens cavity can be changed by applying a voltage across the lens cavity, whereby a lens with variable focus is realised.

Figure 3:
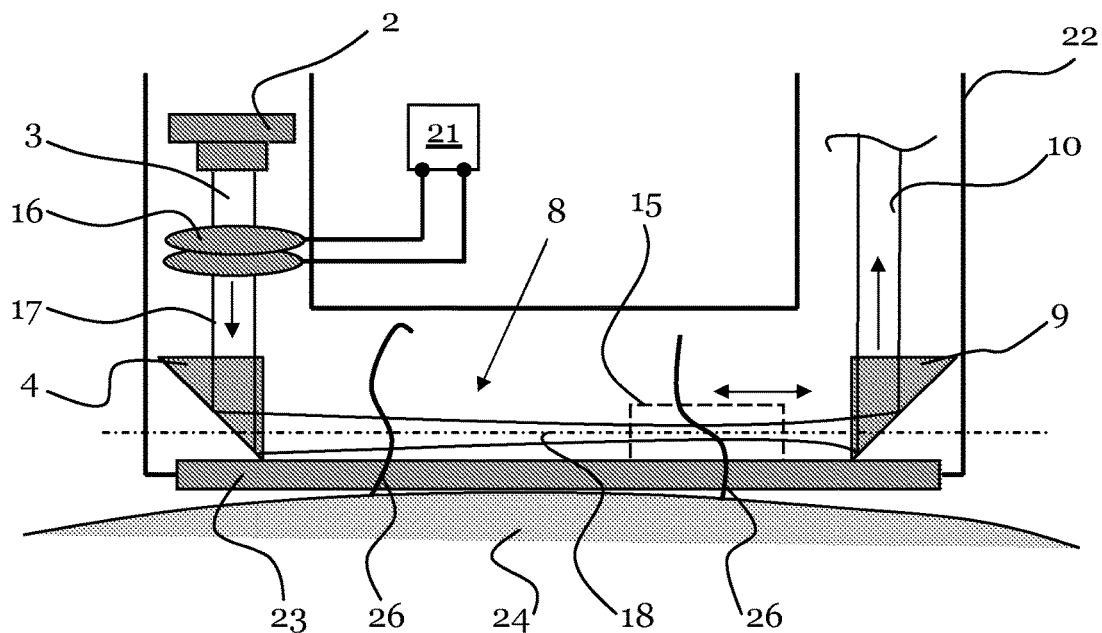
FIG. 3 shows a schematic diagram of the optical system for the cutting head of FIG. 2 against the skin of a user.

FIG. 3 shows a schematic view of a cutting head of a laser shaver comprising the optical system of FIG. 2. The cutting head comprises a body 22 with a spacer 23 that contacts the skin 24 to maintain protective separation between the laser beam 18 and the skin 24. The spacer 23 comprises at least one opening to allow hairs 26 to protrude into the cutting zone 8, which is defined in the region above the spacer 23 where the cutting laser beam 18 crosses. The spacer 23 may comprise a single, elongate opening that is parallel to the cutting laser beam through which hairs are received for cutting. The spacer 23 may instead comprise a plurality of circular, hexagonal or similar openings through which the hair is received into the cutting zone 8. Alternatively, the spacer 23 may comprise a comb with a plurality of teeth that manipulate the hairs into the cutting zone.

The first and second reflective elements 4, 9 are positioned on opposite sides of the body 22 and the diode 2 and variable focus lens 16 are positioned on one side of the body 22, aligned with the first reflective element 4.

As shown in FIG. 3, hairs 26 protrude from the skin 24 and are received through the spacer 22 into the cutting zone 8 where the hairs are intersected by the cutting laser beam 18 that is substantially parallel to the surface of the skin 24. The high intensity region 15 of the laser beam 18 is moved back and forth across the cutting zone 8, along the optical axis 12 by varying the focal point of the variable focus lens 16 as described with reference to FIG. 2. Therefore, any hairs 26 received through the spacer and in the cutting zone 8 as the shaver is moved across the skin 24 will be subject to the high intensity region 15 of the laser beam 18 as it moves back and forth along the optical axis, thereby severing the hairs. The controller 21 may be configured to move the high intensity region 15 back and forth across the cutting zone 8, along the optical axis 12 at a sufficient rate to ensure all hairs are exposed to the high intensity portion 15 and severed during normal movement of the shaver across the skin 24.

Figure 4:
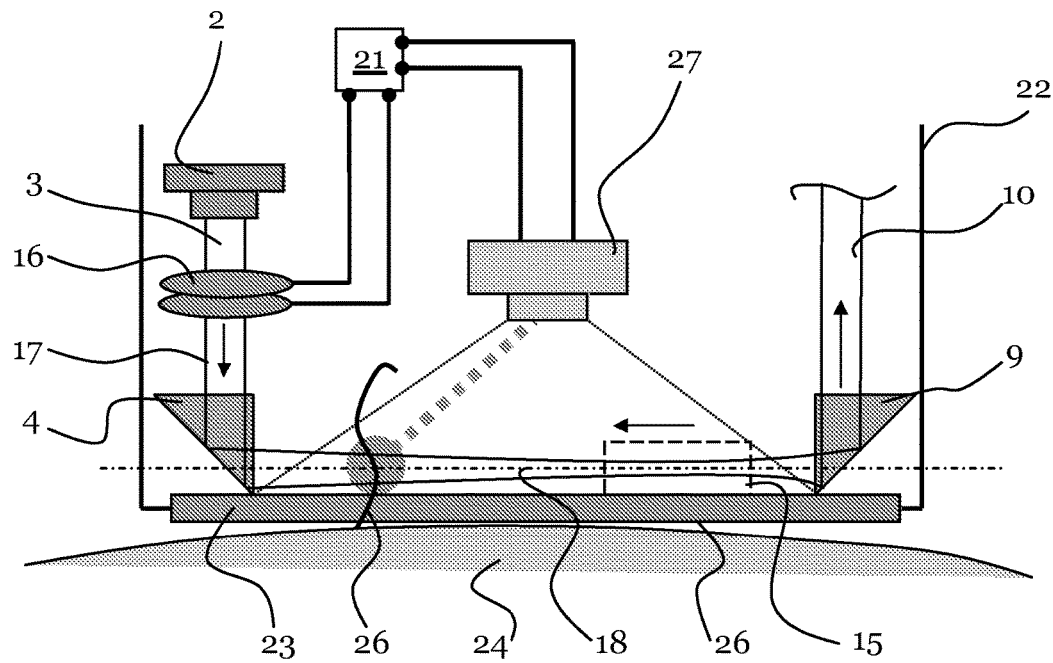
FIG. 4 shows a schematic diagram of the optical system for the cutting head of FIG. 3, further comprising a hair detector.

FIG. 4 shows another embodiment of the invention, further comprising a hair detector 27, such as a vision system, proximity sensor or any other sensor. The hair detector is configured to identify the position of hairs 26 protruding through the spacer 23 and entering the cutting zone 8. The hair detector 27 communicates with the controller 21 which is configured to control the variable focus lens 16 such that the high intensity region 15 of the cutting laser beam is moved to coincide with the position of the detected hair, thereby severing that hair.

Figure 5:
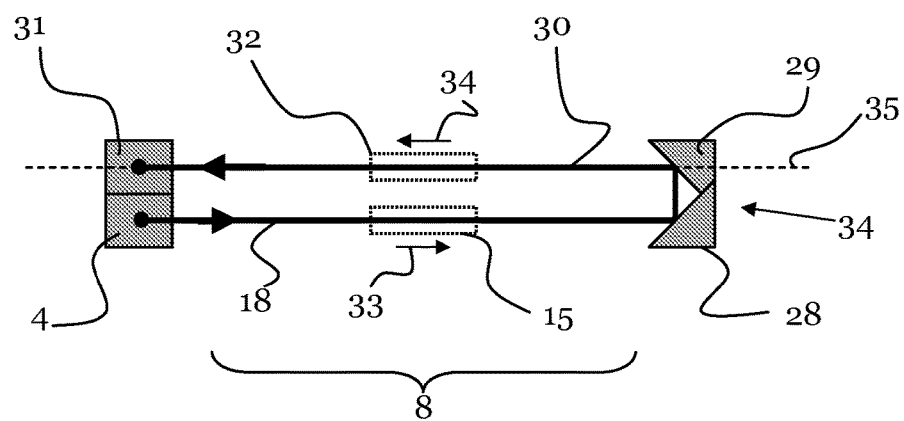
FIG. 5 shows a top view schematic diagram of an optical system for a laser cutting head comprising multiple cutting beams; and, FIG. 6 shows a schematic diagram of a laser shaver with a detachable cutting head.

The applicant's previous application WO 2010/106480 A1 provides a more detailed description of a device and a method for detecting hairs on a surface. FIG. 5 shows a top view schematic diagram of another embodiment of the invention. The lines representing the laser beams 18, 30 are only representative of the direction of the laser beams and do not show the Gaussian intensity distributions, which would be present. FIG. 5 shows the first reflective element 4 which reflects the first cutting laser beam 18 across the cutting zone 8. The high intensity region 15 is shown in the center of the cutting zone 8. In this embodiment, the second reflective element 34 comprises two portions 28, 29 configured to reflect the cutting laser beam 18 back across the cutting zone 8, to create a second cutting beam 30 that passes through the cutting zone 8, therefore improving the cutting performance of the shaver. The cutting beam 18 may be reflected along a second optical axis 35 in the cutting zone 8 such that there are two parallel adjacent cutting beams 18, 30 across the cutting zone 8. Alternatively, the second cutting beam may be at an angle to the first cutting beam.

The second reflective element 34 may be configured to focus the second cutting beam 30 within the cutting zone 8 as shown in FIG. 5. For example, when the high intensity region 15 of the first cutting beam 18 is at the center of the cutting zone 8, the reflective element 34 is configured such that the high intensity region 32 of the second cutting beam 30 is also at the center of the cutting zone 8. To focus the second cutting beam 30, an additional variable focus lens (not shown) may be positioned adjacent to the second reflective element 34.

Alternatively, the first variable focus lens 16 (see FIGS. 2 and 3) can be used to alter the position of the high intensity region 15 of the first cutting beam 18 and the position of the high intensity region 32 of the second cutting beam 30 simultaneously. For example, when the high intensity region 15 of the first cutting beam 18 is at the center of the cutting zone 8 and the second reflective element 34 is configured to focus the second cutting beam 30 so that the high intensity region 32 is also at the center of the cutting zone 8, a motion of the high intensity region 15 of the first cutting beam 18 towards the second reflector 34, indicated by arrow 33, will cause the high intensity region 32 of the second cutting beam 30 to move towards the first reflector 4, as indicated by arrow 34. Therefore, hairs close to the second and first reflectors 34, 4 are efficiently cut by the first cutting beam 18 and the second cutting beam 30 respectively.

Optionally, additional subsequent reflective elements (not shown) may be used to reflect the laser beam back across the cutting zone 8 multiple times, allowing the beam to pass for a third, fourth and fifth times across the cutting zone. This will improve the cutting performance of the shaver still further.

Figure 6:
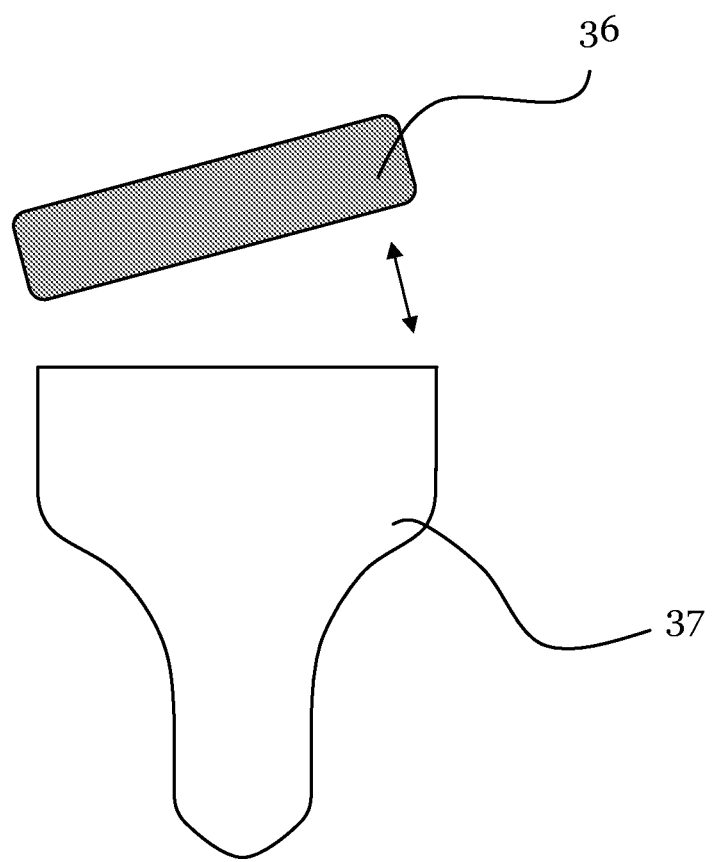

It will be appreciated that the cutting head described with reference to any of FIGS. 2, 3, 4 and 5 may be a separate cutting head unit 36 that is attachable to a shaver handle 37, as shown in FIG. 6. The cutting head unit 36 may be removed to clean the cutting head or to replace the cutting head or components of the cutting head after they have become worn.

The components described, in particular the variable focus lens (16), laser beam generator (2) and controller (21), may be located either in the detachable cutting head 36 or in the handle 37 of the shaver. Alternatively, the cutting head 36 may be integrated with a shaver handle 37 as one product (not shown).

The shaving device described with reference to FIGS. 2 to 6 relates to shaving the skin to achieve a minimum remaining hair length as well as improved uniformity of remaining hair length. However, the device for cutting hair defined in the claims may alternatively be used for trimming hair to a controlled length that is not necessarily as short as possible, as is the case with a hair trimming or grooming device. To achieve this, the guard would be positioned further from the cutting laser beam(s) so that the cutting height is increased, but remains uniform.

It will be appreciated that the term "comprising" does not exclude other elements or steps and that the indefinite article "a" or "an" does not exclude a plurality. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

Other modifications and variations falling within the scope of the claims hereinafter will be evident to those skilled in the art.

The invention claimed is:

1. A hair cutting device head comprising:
   an optical system comprising:
      a variable focus lens configured to:
         focus a laser beam to a focal point;
      a first reflective element configured to:
         receive the laser beam; and
         re-direct said laser beam along a first optical axis within a cutting zone substantially parallel to a skin portion of a user;
      a second reflective element positioned on a side of the cutting zone opposite to the first reflective element, said second reflective element configured to:
         direct the laser beam back across the cutting zone along a second optical axis substantially parallel to the first optical axis within the cutting zone; and
      a controller configured to:
         vary characteristics of the variable focus lens to alter a position of the focal point of the laser beam within the cutting zone,
         wherein the focal point of a laser beam within the cutting zone is moved along the first optical axis of the re-directed laser beam in an oscillating motion.

2. The hair cutting device head according to claim 1, wherein a position of the focal point is not altered, for a predetermined period of time, during alteration of the position of the focal point.

3. The hair cutting device head according to claim 1, further comprising:
   a laser beam generator configured to:
      generate the laser beam, wherein the variable focus lens is positioned between the laser beam generator and the first reflective element.

4. The hair cutting device head according to claim 1, further comprising:
   a spacer, positioned adjacent to the cutting zone, said spacer maintaining a spacing between the skin portion of the user and the optical axis of the laser beam in the cutting zone.

5. The hair cutting device head according to claim 1, wherein
   said second reflective element configured to direct the laser beam away from the cutting zone.

6. The hair cutting device head according to claim 1, wherein the variable focus lens is selected from a group consisting of: mechanically actuated, fluid focus, liquid crystal, and electrophoretic.

7. The hair cutting device head according to claim 4, wherein the spacer includes at least one opening.

8. The hair cutting device head according to claim 7, wherein the at least one opening is one of: elongated, circular, and hexagonal.

9. The hair cutting device head according to claim 4, wherein the spacer comprises a comb comprising a plurality of teeth.

10. A device for cutting hair, comprising:
    at least one cutting head comprising:
       an optical system comprising:
          a variable focus lens configured to:
             focus the laser beam to a focal point;
          a first reflective element configured to:
             direct the laser beam along a first optical axis within a cutting zone of said at least one cutting head,
          a second reflective element positioned on a side of the cutting zone opposite to the first reflective element, said second reflective element configured to:
             direct the laser beam back cross the cutting zone along a second optical axis substantially parallel to the first optical axis within the cutting zone; and
          a controller configured to:
             control a variation of a characteristic of the variable focus lens to alter a position of the focal point along the first optical axis of the laser beam within the cutting zone in an oscillating manner.

11. The device according to claim 10, wherein the controller is configured to:
    control the position of the focal point.

12. The device for cutting hair according to claim 10, wherein the controller is configured to:
    maintain a dwell time of the focal point at a position along the optical axis substantially constant.

13. The device for cutting hair, according to claim 10, further comprising a hair sensor configured to:
    detect a position of a hair in the cutting zone, wherein the controller is configured to:
       receive the detected position of the hair; and
       position the focal point of the laser beam to coincide with said detected hair position.

14. The device for cutting hair according to claim 13, wherein the hair sensor is selected from a group consisting of: a vision system and a proximity sensor.

15. A method of controlling a device for cutting hair, comprising the steps of:
    directing, a laser beam in a first direction across a cutting zone substantially parallel to a surface containing said hair,
    directing said laser beam, in a second direction, opposite the first direction, substantially parallel to the laser beam in the first direction within the cutting zone; and
    varying a characteristic of a variable focus lens to position a focal point of the laser beam along the optical axis, wherein the characteristic of the variable focus lens is varied to cause the focal point to move in an oscillating manner.

* * * * *